United States Patent [19]

Van Leeuwen et al.

[11] 4,330,678
[45] May 18, 1982

[54] PROCESS FOR THE HYDROFORMYLATION OF OLEFINS

[75] Inventors: Petrus W. N. M. Van Leeuwen; Cornelis F. Roobeek, both of Amsterdam, Netherlands

[73] Assignee: Shell Oil Company, Houston, Tex.

[21] Appl. No.: 213,971

[22] Filed: Dec. 8, 1980

[30] Foreign Application Priority Data

Feb. 4, 1980 [GB] United Kingdom ............... 8003616

[51] Int. Cl.³ .................. C07C 45/50; C07C 47/02
[52] U.S. Cl. ............................. 568/454; 568/882; 568/909
[58] Field of Search ................. 568/454, 909, 882

[56] References Cited

U.S. PATENT DOCUMENTS

| | | | |
|---|---|---|---|
| 3,849,359 | 1/1975 | Keblys | 568/454 |
| 3,917,661 | 11/1974 | Pruett et al. | 568/454 |
| 4,152,344 | 5/1979 | Unruh | 568/454 |
| 4,221,744 | 9/1980 | Unruh | 568/454 |
| 4,230,641 | 10/1980 | Bartish | 568/454 |

OTHER PUBLICATIONS

Pruett et al., "J. Organic Chem.", vol. 34, No. 2 (1969), pp. 327-330.

*Primary Examiner*—Werren B. Lone

[57] ABSTRACT

A process for the hydroformylation of an olefin which comprises reacting an olefin with carbon monoxide and hydrogen in the process of a complex of rhodium with a compound of the formula:

$$L(OR^1)(OR^2)(OR^3)$$

wherein L is P or As and $R^1$, $R^2$ and $R^3$ are (dis)similar alkyl, aryl, alkaryl or aralkyl groups, provided that at least one of $R^1$, $R^2$ or $R^3$ represents a group $-CH_n$$[CFXY]_{3-n}$, wherein n is 1 or 2 and either
(a) X and Y both represent F, or
(b) one of X and Y represents F and the other represents H or Cl or an (un)substituted (ar)alkyl group, or
(c) X represents H or Cl or an (un)substituted (ar)alkyl group and Y represents an (ar)alkyl group whose connecting carbon atom carries at least one F.

13 Claims, No Drawings

PROCESS FOR THE HYDROFORMYLATION OF OLEFINS

FIELD OF THE INVENTION

This invention relates to the hydroformylation of olefins utilizing as a catalyst rhodium complexed with fluorine-containing organic phosphites and/or arsenites.

BACKGROUND OF THE INVENTION

Hydroformylation of olefins with the aid of rhodium catalysts is generally known (see, e.g., The Journal of Organic Chemistry, Vol. 34, No. 2, pp. 327–330, and U.S. Pat. Nos. 3,859,359 and 3,917,661).

From the prior art it is also known that phosphorous- or arsenic-containing ligands have a considerable effect on the ratio of the amounts of normal aldehydes and branched-chain aldehydes. The article of Pruett and Smith in The Journal of Organic Chemistry, Vol. 34, No. 2, pp. 327-330 teaches that generally in the hydroformylation of oct-1-ene with tri-substituted phosphorus-containing ligands, an aliphatic substituent gives a lower percentage of straight-chain (or normal) aldehyde than an aromatic substituent. This is in conformity with the numerous experiments disclosed by Pruett and Smith in U.S. Pat. No. 3,917,661 and the ΔHNP value-theory in Table A. In the U.S. Pat. No. 3,917,661 is likewise disclosed as a suitable ligand, tri(p-chlorophenyl)phosphite, giving a high percentage of normal aldehydes from α-olefins. Other examples of ligands are tri-m-fluorophenyl phosphite are tri-m-trifluoromethyl-phenyl phosphite, as mentioned in U.S. Pat. No. 3,859,359; however, no details on the amount of normal aldehydes are given. But special attention is given for a preferred hydroformylation process, using phenyl group-containing phosphites as ligands (see column 8, lines 34–47).

Applicant has now found a specific group of fluorine containing organic phosphites and arsenites as ligands which give even higher percentage of normal aldehydes from α-olefins, but surprisingly also from β- and other internal olefins.

SUMMARY OF THE INVENTION

This invention relates to a process for the hydroformylation of an olefin which comprises reacting an olefin with carbon monoxide and hydrogen in the presence of a complex of rhodium with a compound of the formula:

$$L(OR^1)(OR^2)(OR^3)$$

wherein L is P or As and $R^1$, $R^2$ and $R^3$ are (dis)similar alkyl, aryl, alkaryl or aralkyl groups, provided that at least one of $R^1$, $R^2$ or $R^3$ represents a group —$CH_n[CFXY]_{3-n}$, wherein n is 1 or 2 and either (a) X and Y both represent F, or
(b) one of X and Y represents F and the other represents H or Cl or an (un)substituted (ar)alkyl group, or
(c) X represents H or Cl or an (un)substituted (ar)alkyl group and Y represents an (ar)alkyl group whose connecting carbon atom carries at least one F.

It is quite unexpected that the ligand containing as $R^1$, $R^2$ and/or $R^3$ the aliphatic group

—$CH_n[CFXY]_{3-n}$ gives such a high percentage of normal aldehydes from α-olefins as well as from β-olefins and other internal olefins. Preferred ligands are those containing end-$CF_3$-groups. Examples of preferred ligands are those having the chemical formula $P(OCH_2CF_3)_3$, $P(OCH_2CF_2CF_3)_3$ and

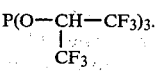
$P(O-CH-CF_3)_3$.
   |
   $CF_3$

DESCRIPTION OF THE ILLUSTRATIVE EMBODIMENTS

Generally the hydroformylation of the olefin is carried out under rather mild conditions. The temperature may be in the range of from about 50° to about 200° C. and preferably from about 80° to about 130° C. The pressure, which is the sum of hydrogen and carbon monoxide pressure, is preferably in the range of from about 3 to about 35 bar, although lower or higher pressures are not excluded.

Generally the mol. ratio of hydrogen to carbon monoxide is in the range of from about 1:2 to about 12:1.

The amount of catalyst may vary within wide ranges, but generally the mol. ratio of catalyst to olefin is in the range of from about 1:10000 to about 1:10. The rhodium catalyst which is a complex of rhodium and ligand may be formed from 1,5-cyclo-octadiene-rhodium(I) acetate or any other rhodium source. (1,5-Cyclo-octadiene-rhodium(I) acetate occurs in the form of the dimer. In the Examples the calculations were made as if it is a monomer).

Suitable starting materials are olefins, especially α-olefins with up to about 30 carbon atoms, preferably up to about 10 carbon atoms. Examples are propylene, butene-1, pentene-1, hexene-1, heptene-1, octene-1, nonene-1, decene-1 and dodecene-1 and their isomers-2, -3, or -4.

Preferred solvents used in the hydroformylation are hydrocarbons, such as benzene, toluene, cyclohexene or methylcyclohexane.

The compounds prepared by the hydroformylation process are aldehydes under these mild conditions. When starting from α-olefins, the α-olefins may be partly isomerized to β-olefins. The amount of straight-chain aldehydes (also called normal aldehydes) is generally very high and under comparable circumstances higher than when as ligands tri(p-chlorophenyl)-phosphite or tri(m-trifluoromethylphenyl)phosphite are used.

When starting from β-olefins (or other internal olefins) high proportions of linear products are also obtained. The catalysts used in the process according to our invention show a preference for terminal hydroformylation. It was quite unexpected that β-olefins (or other internal) olefins give end-products with high linearity, as has been deomonstrated in Examples 6–8.

The process of the instant invention is particularly directed to hydroformylating olefins to a high percentage of normal aldehydes wherein alpha olefins are converted to normal aldehydes with selectivities greater than about 90 percent and internal olefins are converted to normal aldehydes with selectivities greater than about 30 percent.

The process will be further illustrated by the following examples which are provided for illustration and are not to be construed as limiting the invention.

EXAMPLE 1

A 100 ml stainless steel autoclave was charged with 20 ml benzene, in which were dissolved 0.01 mmol. of 1,5-cyclo-octadiene-rhodium(I)acetate and 0.2 mmols of a phosphite of the chemical formula $P(OCH_2CF_3)_3$, under an atmosphere of argon and the autoclave was also charged with 10 mmols of hept-1-ene. The autoclave was then pressurized with a 1:1 mol. mixture of hydrogen and carbon monoxide and heated to 95° C., the pressure in the autoclave being now 9.5 bar. After 2 hours at the reaction temperature of 95° C., the autoclave was cooled to ambient temperature and the gases were vented in a fume cupboard. A pale yellow liquid remained in the autoclave.

The resulting pale yellow liquid was analyzed by gas-chromatography and the constituents were identified by GC and NMR by comparison with authentic samples.

The conversion of hept-1-ene was 66%, and the product consisted of 96% n-octaldehyde.

A number of examples 2–11 are given with different ligands, using the same method as described above. Comparative examples are likewise included. Unless otherwise stated in the Table the reaction conditions are the same as those applied in the above Example 1. The designation $\phi$ in the chemical formulae means a phenyl group.

$$L(OR^1)(OR^2)(OR^3)$$

wherein L is P or As and $R^1$, $R^2$ and $R^3$ are (dis)similar alkyl, aryl, alkaryl or aralkyl groups, provided that at least one of $R^1$, $R^2$ or $R^3$ represents a group $-CH_n[CFXY]_{3-n}$, wherein n is 1 or 2 and either (a) X and Y both represent F, or
(b) one of X and Y represents F and the other represents H or Cl or an (un)substituted (ar)alkyl group, or
(c) X represents H or Cl or an (un)substituted (ar)alkyl group and Y represents and (ar)alkyl group whose connecting carbon atom carries at least one F, which hydroformylation reaction is carried out at a temperature in the range of from about 50° C. to about 200° C.

2. The process of claim 1 wherein the complex is a complex of rhodium with $P(OCH_2CF_3)_3$.

3. The process of claim 1 wherein the complex is a complex of rhodium with:

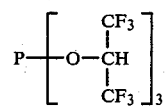

4. The process of claim 1 wherein the complex is a complex of rhodium with $P(OCH_2CF_2CF_3)_3$.

5. The process of claim 1, 2, 3 or 4 wherein the temperature is in the range of from about 80° C. to about 130° C.

6. The process of claims 1, 2, 3 or 4 wherein the sum of the pressures of hydrogen and carbon monoxide ranges from about 3 to about 35 bar.

7. The process of claims 1, 2, 3 or 4 wherein the mol. ratio of hydrogen to carbon monoxide is in the range of from about 1:2 to about 12:1.

TABLE

| EX | Ligand | P/Rh atom ratio | m.mol Rh(COD)OAc | heptene 1 or 2 | temperature in °C. | pressure (bar) | H₂/CO mol ratio |
|---|---|---|---|---|---|---|---|
| 1 | $P(OCH_2CF_3)_3$ | 20 | 0.01 | 1 | 95 | 9.5 | 1/1 |
| 2 | $P(OCH_2CF_3)_3$ | 4 | 0.01 | 1 | 95 | 9.5 | 1/1 |
| 3 | $P(OCH_2CF_2CF_3)_3$ | 4 | 0.01 | 1 | 95 | 12 | 2/1 |
| 4 | $P(O\phi mCF_3)_3$ | 10 | 0.02 | 1 | 95 | 14 | 1/1 |
| 5 | $P(O\phi pCl)_3$ | 20 | 0.01 | 1 | 95 | 9.5 | 1/1 |
| 6 | $P(OCH_2CF_3)_3$ | 3 | 0.01 | 2 | 90 | 9.5 | 1/1 |
| 7 |  | 2 | 0.01 | 2 | 90 | 9.5 | 1/1 |
| 8 | $P(OCH_2CF_3)_3$ | 9 | 0.02 | 2 | 120 | 9.5 | 1/1 |
| 9 | $P(OCH_2CH_3)_3$ | 9 | 0.02 | 2 | 120 | 9.5 | 1/1 |
| 10 | $P(OCH_2CF_3)_3$ | 9 | 0.01 | * | 90 | 10 | 1/1 |
| 11 | $P(O\phi pCl)_3$ | 9 | 0.01 | * | 90 | 10 | 1/1 |

| EX | conversion in % | reaction rate moles/mol Rh/hour | reaction time in hrs. | % isomerisation | linearity of the aldehyde in % | selectivity to total aldehyde in % |
|---|---|---|---|---|---|---|
| 1 | 66 | 300 | 2 | 35 | 96 | 65 |
| 2 | 100 | 1500 | 0.5 | 27 | 90 | 73 |
| 3 | 95 | — | 0.2 | 50 | 95 | 47 |
| 4 | 100 | 1500 | 0.5 | 35 | 87 | 65 |
| 5 | 66 | — | 0.5 | 22 | 86 | 78 |
| 6 | 50 | — | 1 | n.a. | 37 | 99 |
| 7 | 30 | — | 1 | n.a. | 42 | 99 |
| 8 | 10 | — | 1 | n.a. | 62 | 99 |
| 9 | 18 | — | 2 | n.a. | 8 | 99 |
| 10 | 30 | — | 1 | n.a. | 85 | 100 |
| 11 | 90 | — | 1 | n.a. | 67 | 100 | n.a. not applicable
* propene instead of heptene

What is claimed is:

1. A process for the hydroformylation of an olefin to a high percentage of normal aldehydes which comprises reacting an olefin with carbon monoxide and hydrogen in the presence of a complex of rhodium with a compound of the formula:

8. The process of claims 1, 2, 3 or 4 wherein the mol. ratio of catalyst to olefin is in the range of from about 1:10000 to about 1:10.

9. The process of claims 1, 2, 3 or 4 wherein the reaction is carried out in a hydrocarbon solvent.

10. The process of claims 1, 2, 3 or 4 wherein the reaction is carried out in a hydrocarbon solvent and the solvent is benzene.

11. The process of claims 1, 2, 3 or 4 wherein the olefin is an alpha-olefin.

12. The process of claims 1, 2, 3 or 4 wherein the olefin is an internal olefin.

13. The process of claims 1, 2, 3 or 4 wherein the olefin is a beta-olefin.

* * * * *